United States Patent [19]
Nomura et al.

[11] Patent Number: 5,100,553
[45] Date of Patent: Mar. 31, 1992

[54] METHOD FOR TREATING ORGANIC WASTE BY METHANE FERMENTATION

[75] Inventors: Tadashi Nomura, Handa; Mitsuo Kawase, Chita; Naoki Murata, Nagoya, all of Japan

[73] Assignee: NGK Insulators, Ltd., Japan

[21] Appl. No.: 570,042

[22] Filed: Aug. 20, 1990

[30] Foreign Application Priority Data

Aug. 25, 1989 [JP] Japan .................. 1-219469
Jun. 5, 1990 [JP] Japan .................. 2-146842

[51] Int. Cl.⁵ .................................. C02F 3/28
[52] U.S. Cl. ........................... 210/610; 210/615; 210/631
[58] Field of Search ............. 210/603, 605, 609–611, 210/613–618, 630, 631

[56] References Cited

U.S. PATENT DOCUMENTS

| | | | |
|---|---|---|---|
| 4,200,523 | 4/1980 | Balmat | 210/631 |
| 4,297,122 | 10/1981 | Wallace | 210/610 |
| 4,351,729 | 9/1982 | Witt | 210/603 |
| 4,614,587 | 9/1986 | Andersson et al. | 210/603 |
| 4,789,478 | 12/1988 | Revis et al. | 210/611 |
| 4,861,519 | 8/1989 | Tusa et al. | 210/603 |

OTHER PUBLICATIONS

"Nickel Stimulation of Anaerobic Digestion", Water Research, vol. 17, No. 6, 1983, pp. 677–682, R. E. Speece et al.
"Effect of Nickel on Bilogical Methane Generation from a Laboratory Poultry Wast Digester", Biotechnology & Bioengineering, vol. 28, No. 11, Nov. 1986, pp. 1608–1610, C. M. Williams et al.
Patent Abstracts of Japan, vol. 14, No. 356 (C-745) [4299], Aug. 2, 1990, JP-A-2 131 196 (Kubota Ltd.) 18-5-90.
Patent Abstracts of Japan, vol. 13, No. 56 (C-566) [3404], Feb. 8, 1989, JP-A-63 248 497 (NGK Insulators Ltd.) 14-10-88.
Biotechnology Letters, vol. 3, No. 4, 165–170 (1981); "Support Materials for Stationary Fixed Film Reactors for High-Rate Methanogenic Fermentations."
Wat. Sci. Tech. vol. 21, Brighton, pp./77–86, 1989, "An Anaerobic Fixed Bed Reactor with a Porous Ceramic Carrier."
"Mineral Nutrient Requirements for High-Rate Methane Fermentation of Acetate at Low SRT," Nov./Dec. 1989 pp. 1645–1650.

*Primary Examiner*—Thomas Wyse
*Attorney, Agent, or Firm*—Parkhurst, Wendel & Rossi

[57] ABSTRACT

Proliferation activity of methane bacteria in organic waste water can be improved by maintaining the ratio of the amounts of nickel, iron and cobalt contained in the waste water to the BOD thereof to not lower than certain values, and various organic waste waters, such as waste liquor formed during the production of beer and the like, can be treated in a high BOD removal ratio of not lower than 90% while maintaining a high BOD load of not lower than 10 kg/m³·day.

5 Claims, 6 Drawing Sheets

FIG_2

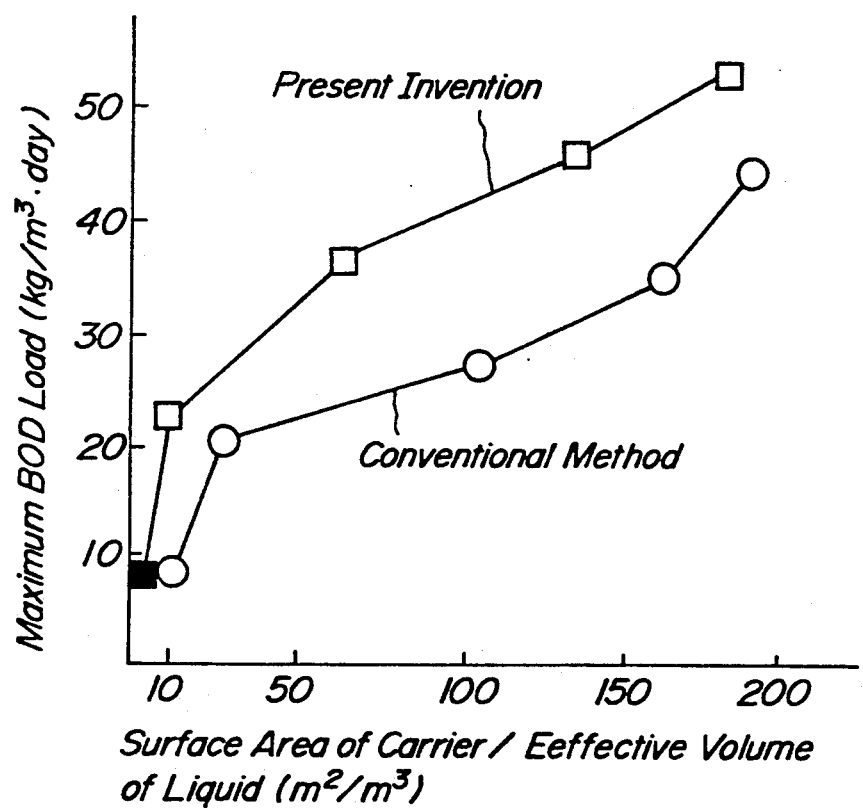
FIG_6

METHOD FOR TREATING ORGANIC WASTE BY METHANE FERMENTATION

BACKGROUND OF THE INVENTION

1) Field of the Invention

This invention relates to a method for treating organic waste water by the methane fermentation, which method is adapted for treating organic waste water, such as waste liquor formed in the production step of beer or the like, through a biological treatment by the use of mesophilic or thermophilic methane bacteria, and an apparatus to be used for method.

2) Related Art Statement

As the above described treating method of organic waste water, there are known an aerobic treatment using of active sludge and an anaerobic treatment by the use of methane bacteria. Recently, there has been noticed a treating method, wherein an organic substance is decomposed into methane gas and carbon dioxide with the use of mesophilic or thermophilic methane bacteria by means of an anaerobic fixed bed. However, in the case where an alcohol waste liquor, such as waste liquor formed in the production step of beer, is treated by the methane fermentation, when the BOD load is as low as about 1-3) $kg/m^3 \cdot day$, the treatment can be effected without trouble, but when the BOD load is higher than about 3 $kg/m^3 \cdot day$, the BOD removal ratio is gradually lowered, and a satisfactorily high treating effect can not be obtained.

Japanese Patent Laid-open Application No. 64-47,498 discloses a method for improving the efficiency of methane fermentation by adding a mineral and a nutrient, such as amino acid or the like, to alcohol waste liquor. However, the inventors have tested this method in a practical operation and have concluded that this method is still unsatisfactory in the BOD load and BOD removal.

According to the investigation by the inventors, in the treating apparatus using an anaerobic fixed bed of this kind, its treating ability is highly influenced by the value of the ratio of the apparent surface area of the carrier, which carries a microorganism thereon, to the effective volume of the anaerobic treating apparatus. That is, in the anaerobic treatment, the BOD contained in waste water is decomposed into organic acid (through acid fermentation) by the action of acid fermentation bacteria contained in the liquid phase, and the resulting organic acid is decomposed into methane gas by the action of the methane bacteria fixed to the surface of a carrier. Therefore, it is important the methane fermentation in the second half stage proceeds in a rate higher than the rate of the acid fermentation in the first half stage in order for the anaerobic treatment to proceed smoothly. For this purpose, it is necessary that the value of the ratio of the surface area of the carrier, which is the residence of methane bacteria, to the volume of the liquid phase, which is the residence of acid fermentation bacteria, is not lower than a certain value, and it has been necessary that the value of the ratio of (surface area of carrier)/(effective volume of liquid) is at least 20 $m^2/m^3$ as disclosed in Japanese Patent Laid-open Application No. 63-248,497.

SUMMARY OF THE INVENTION

One of the objects of the present invention is to solve the above described problems in the conventional methods and to provide a method for treating organic waste waters by methane fermentation, which can treat organic waste liquors, such as waste liquor formed in the production step of beer and the like, in a high BOD removal ratio of not lower than 90% while maintaining a high BOD load of not lower than 10 $kg/m^3 \cdot day$, and a apparatus to be used for the method.

Another object of the present invention is to provide a method for treating organic waste waters by methane fermentation, which can attain the above described object by means of an apparatus having such a value of the ratio of (surface area of carrier)/(effective volume of liquid) that is considerably lower than the value of the ratio in the conventional method.

The inventors have made various investigations in order to solve the above described problems, and found out that the reason why an increase of the BOD load results in lowering of the BOD removal lies in the lowering of the proliferation speed of methane bacteria due to the shortage of nutrient, and that the use of three elements of nickel, iron and cobalt in amounts fairly larger than the amounts, which have hitherto been considered to be necessary in the conventional method, is necessary for improving the proliferation activity of methane bacteria. The inventors have further ascertained that, when the proliferation activity of methane bacteria, which has been fixed to a carrier, is improved by the addition of these elements to a waste water to be treated, the value of the ratio of (surface area of carrier)/(effective volume of liquid) can be decreased to a value lower than the value which has hitherto been considered to be necessary in the conventional method.

The present invention has been accomplished based on the above described knowledge.

The first aspect of the present invention lies in a method for treating an organic waste water by a methane fermentation with the use of an anaerobic fixed bed, an improvement comprising effecting the treatment in the presence of nickel, iron and cobalt, which are nutrient elements necessary for the proliferation of methane bacteria, while maintaining the amounts of Ni, Fe and Co based on the BOD in the waste water in such amounts that the value of the ratio of Ni/BOD is at least $25 \times 10^{-6}$, the value of the ratio of Fe/BOD is at least $60 \times 10^{-6}$ and the value of the ratio of Co/BOD is at least $1.25 \times 10^{-6}$.

The second aspect of the present invention lies in that the treatment of the above described first aspect of the present invention is carried out by means of an anaerobic treating apparatus containing a carrier packed therein, and having a value of the ratio of the apparent surface area of the carrier to the effective volume of the apparatus (the ratio of (surface area of carrier)/(effective volume of liquid)) of at least 10 $m^2/m^3$.

The third aspect of the present invention lies in an anaerobic treating apparatus to be used for carrying out the method of the above described first aspect of the present invention, which apparatus contains a carrier packed therein and has a value of the ratio of the apparent surface area of the carrier to the effective volume of the apparatus (the ratio of (surface area of carrier)/(effective volume of liquid)) of at least 10 $m^2/m^3$.

The term "apparent surface area of a carrier" herein used means the surface area of a carrier, which is calculated from its geometrical shape, and does not include the inner surface area of the carrier material itself, which is formed by fine, small holes, cracks and the like extending into the interior of the carrier material. The term "effective volume of liquid" herein used means the volume obtained by subtracting the volume occupied by the carrier from the volume of the inner space of the apparatus, which receives the waste water therein together with the carrier, that is, means the amount of waste water to be practically treated.

BRIEF DESCRIPTION OF THE DRAWINGS

FIG. 6 is a graph illustrating the relation between the value of the ratio of (surface area of carrier)/(effective volume of liquid) and the maximum BOD load.

DESCRIPTION OF THE PREFERRED EMBODIMENTS

Figure 1:
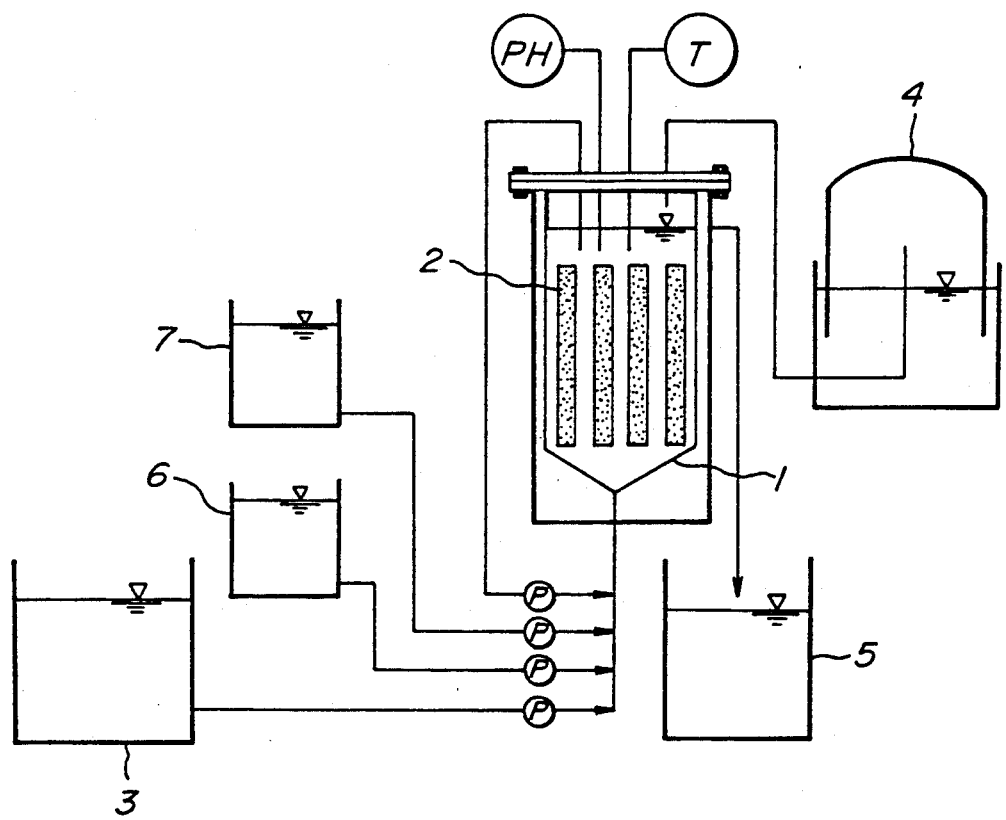
FIG. 1 is a diagrammatical view, partly in section, for explaining the treating method of the present invention.

The present invention will be explained in more detail referring to the drawings.

FIG. 1 illustrates a system to be used for carrying out a methane fermentation treatment of a waste liquor formed in the production step of beer. The numeral 1 represents an anaerobic treating apparatus; the numeral 2 represents a porous ceramics carrier containing a thermophilic methane bacteria deposited thereon; the numeral 3 represents a storage tank for organic waste water; the numeral 4 represents a gas holder for receiving methane gas generated by the methane fermentation; the numeral 5 represents a tank for receiving a treated organic waste water; the numeral 6 represents a storage tank for alkali to be used for maintaining the PH of the organic waste water in the anaerobic treating apparatus 1 to a given PH; the numeral 7 represents a storage tank for nutrient source; the reference PH represents a PH meter; the reference T represents a thermometer; and the reference P represents a pump.

The organic waste waters to be treated in the apparatus of the present invention include waste liquors formed in the production step of beer, such as waste liquor from sludge trub, waste liquor from malt dewatering process, waste beer, waste juice and their mixtures, and the like, and further include whey waste water from soybean process, waste water formed during the distillation in whisky production, and the like. It has been found from the analysis of the components of these waste waters that nickel, iron and cobalt are not at all contained in these waste waters, and even in the case where these elements are contained in the waste waters, the amount is very small.

Therefore, in the present invention, in addition to a commonly known nutrient source supplied from the storage tank 7 for nutrient source, nickel, iron and cobalt are occasionally added to a waste water to be treated. These elements are added to a waste water such that the waste water, after the addition, contains Ni, Fe and Co in amounts, based on the BOD of the waste water, that the value of the ratio of Ni/BOD is at least $25 \times 10^{-6}$, the value of the ratio of Fe/BOD is at least $60 \times 10^{-6}$ and the value of the ratio of Co/BOD is at least $1.25 \times 10^{-6}$. Further, it is preferable to adjust the concentrations of nitrogen and phosphorus in the waste water to be that the value of the ratio of N/BOD is at least $6 \times 10^{-3}$ and the value of the ratio of P/BOD is at least $1.5 \times 10^{-3}$.

The reason why the amounts of nickel, iron and cobalt contained in a waste water are limited to the above described amounts will be explained hereinafter referring to the graphs of FIGS. 2-6, which are compilation of the data with respect to the treatments of waste liquors, which have been formed in the production step of beer, by a thermophilic methane bacteria.

Figure 2:
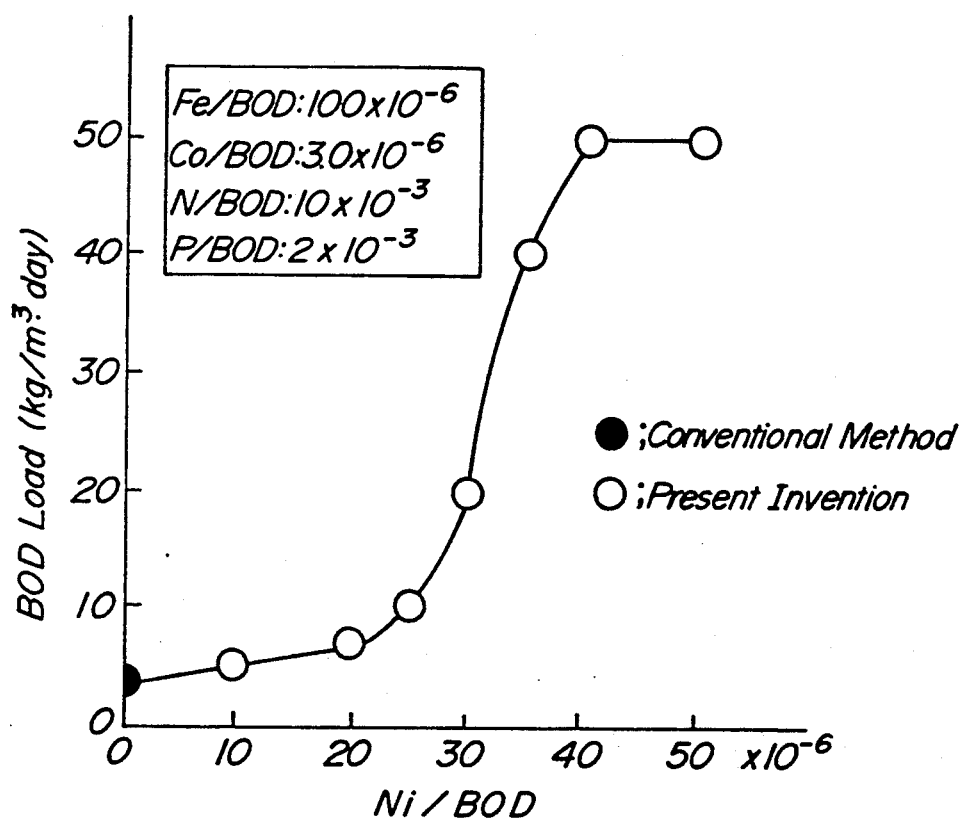
FIG. 2 is a graph illustrating the relation between the value of the ratio of Ni/BOD and the BOD load.
Figure 3:
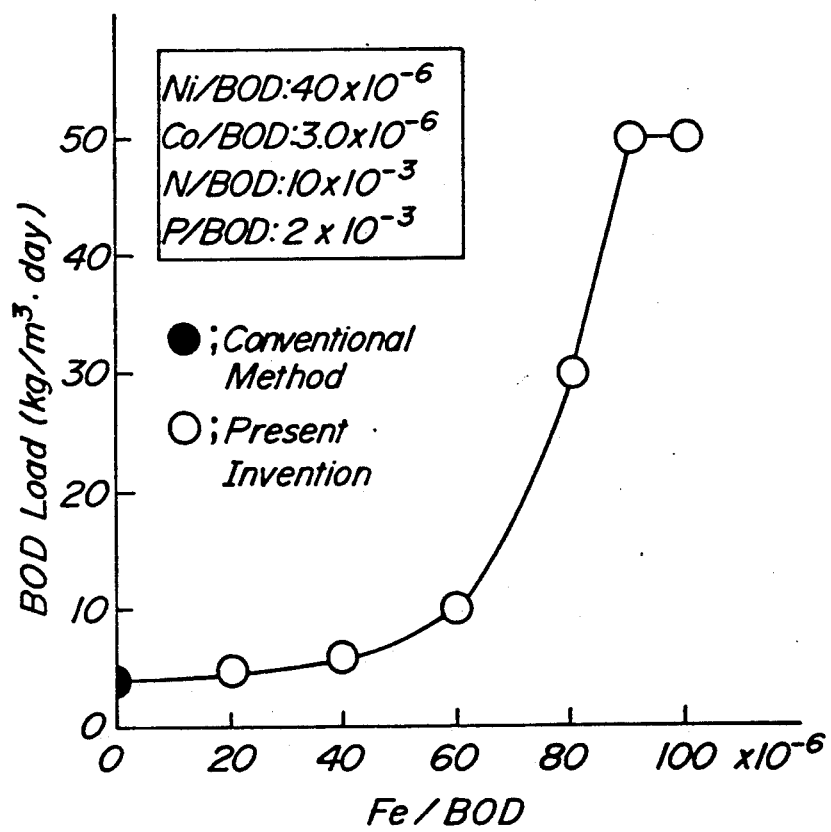
FIG. 3 is a graph illustrating the relation between the value of the ratio of Fe/BOD and the BOD load.
Figure 4:
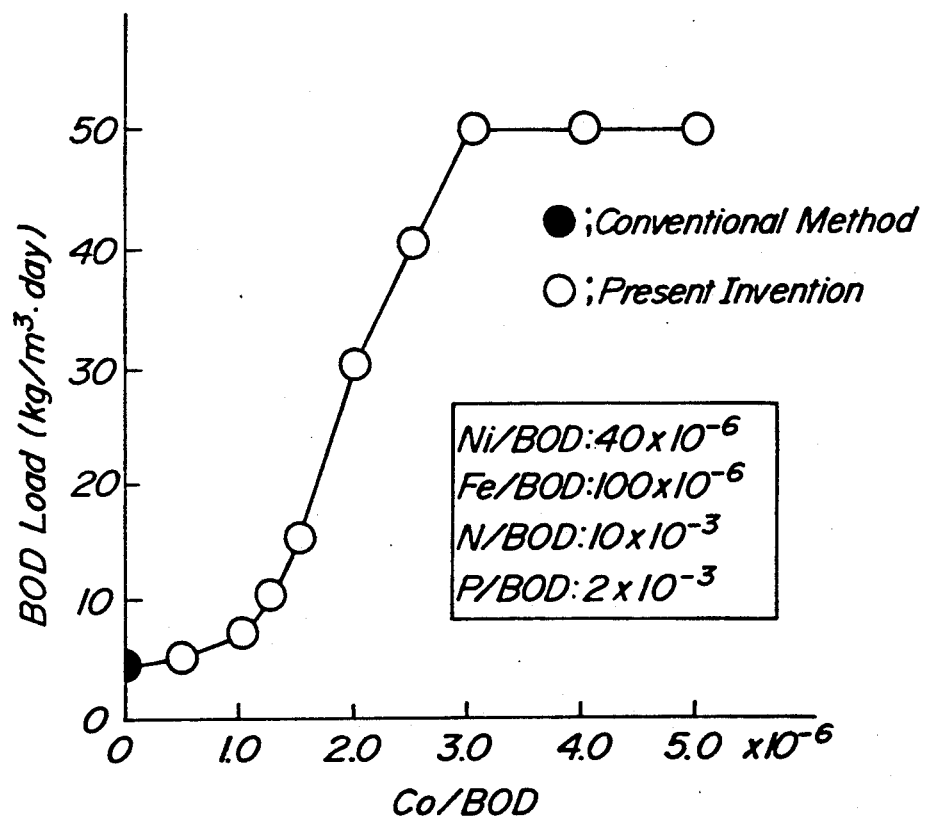
FIG. 4 is a graph illustrating the relation between the value of the ratio of Co/BOD and the BOD load.
Figure 5:
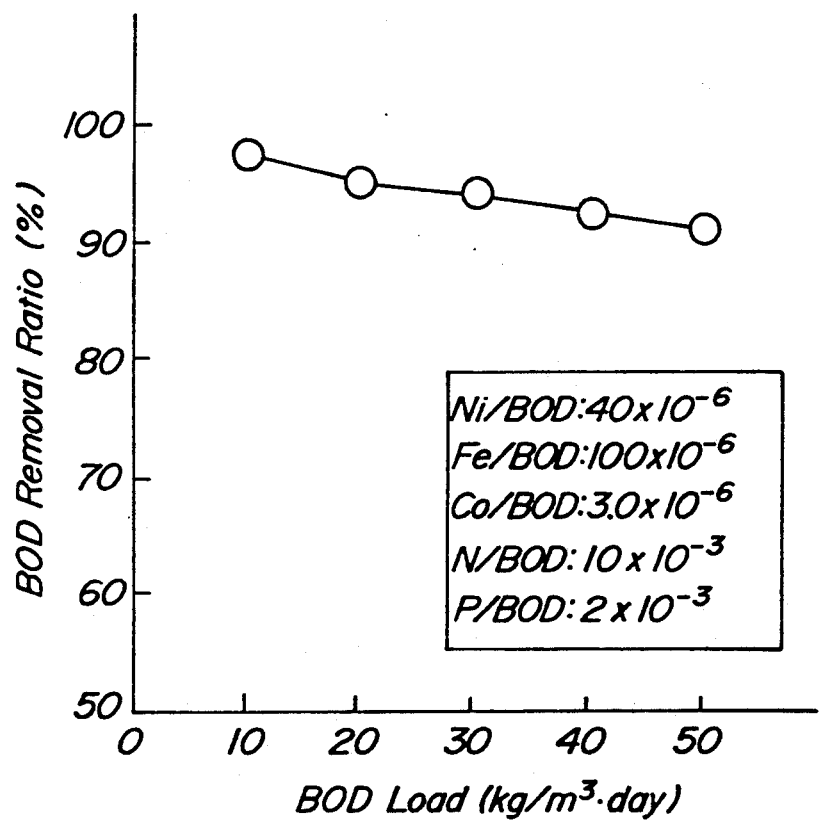
FIG. 5 is a graph illustrating the relation between the BOD load and the BOD removal ratio.

As illustrated in FIG. 2, in the region wherein the value of Ni/BOD is not lower than $25 \times 10^{-6}$, the BOD load exceeds 10 kg/m$^3$·day, but in the region wherein the value of Ni/BOD is lower than $25 \times 10^{-6}$, the BOD load lowers, and in the conventional method, wherein Ni is not at all added to the waste liquor, the BOD load is only about 3 kg/m$^3$·day. FIG. 3 illustrates that, in the region wherein the value of Fe/BOD is not lower than $60 \times 10^{-6}$, the BOD load exceeds 10 kg/m$^3$·day, but in the region wherein the value of Fe/BOD is lower than $60 \times 10^{-6}$, the BOD load lowers as well, and in the conventional method, the BOD load is only about 3 kg/m$^3$·day. Further, as illustrated in FIG. 4, when the value of Co/BOD is not lower than $1.25 \times 10^{-6}$, the BOD load exceeds 10 kg/m$^3$·day.

It has been ascertained that, when the above described conditions are satisfied, a high BOD removal ratio of more than 90% can be attained while maintaining a high BOD load of not lower than 10 kg/m$^3$·day. Further, it has been able to be ascertained that, although these data are ones with respect to thermophilic methane bacteria, data with respect to mesophilic methane bacteria have the same tendency as the data in the thermophilic methane bacteria.

The reason why the addition of such relatively large amounts of nickel, iron and cobalt to a waste water to be treated acts effectively is probably due to the contribution of these elements to the formation of coenzyme during the methane fermentation.

In the above described embodiments, the value of the ratio of the apparent surface area of the porous ceramics carrier 2 packed in an anaerobic treating apparatus 1 to the effective volume of the anaerobic treating apparatus 1 (the ratio of (surface area of carrier)/(effective volume of liquid)) was set to 70 m$^2$/m$^3$. The inventors further measured the maximum BOD load, which was able to be treated by the method of the present invention, by changing variously the value of the ratio of (surface area of carrier)/(effective volume of liquid). This measurement was carried out under a constant condition that the value of Ni/BOD was $50 \times 10^{-6}$, the value of Fe/BOD was $120 \times 10^{-6}$ and the value of Co/BOD was $2.5 \times 10^{-6}$. For comparison, a conventional waste water not added with nickel, iron and cobalt, and having a value of Ni/BOD of $10 \times 10^{-6}$, that of Fe/BOD of $40 \times 10^{-6}$ and that of Co/BOD of $1.0 \times 10^{-4}$ was used, and the maximum BOD load, which was able to be treated with the waste water, was measured in the same manner as described above by changing variously the value of the ratio of (surface area of carrier)/(effective value of liquid). The obtained results are illustrated in FIG. 6.

It can be seen from FIG. 6 that in the conventional method, wherein the values of Ni/BOD, Fe/BOD and Co/NOB are outside the range defined in the present invention, the maximum BOD load is lower than 10 kg/m$^3$·day unless the value of the ratio of (surface area of carrier)/(effective volume of liquid) is at least 20

$m^2/m^3$. On the contrary, in the method of the present invention, even when the value of the ratio of (surface area of carrier)/(effective volume of liquid) is 10 $m^2/m^3$, a high maximum BOD load can be maintained. However, even in the method of the present invention, when the value of the ratio of (surface area of carrier)/(effective volume of liquid) is lower than 10 $m^2/m^3$, the maximum BOD load is lower than 10 kg/$m^3$·day.

As described above, when the values of the ratios of Ni/BOD, Fe/BOD and Co/BOD are within the range defined in the present invention, the methane fermentation ability of methane bacteria fixed to the carrier surface is strengthened, and methane fermentation can be satisfactorily carried out even in the case where the amount of methane bacteria is decreased, and hence even when the value of the ratio of (surface area of carrier)/(effective volume of liquid) is lowered to 10 $m^2/m^3$, the methane fermentation in the second half stage is not adversely influenced by the acid fermentation in the first half stage, and a high BOD load can be maintained.

As clearly understood from the above described explanation, according to the present invention, the ratio of the amounts of nickel, iron and cobalt, which are nutrient elements necessary for the proliferation and the like of methane bacteria, to the BOD are maintained to given values, whereby the proliferation activity of methane bacteria is increased, and various organic waste liquors, such as waste liquor formed in the production step of beer and the like, can be treated in a high BOD removal ratio of not lower than 90% while maintaining a high BOD load of not lower than 10 kg/$m^3$·day. Moreover, according to the apparatus of the present invention, the methane fermentation ability of methane bacteria fixed to the carrier surface has been strengthened, and hence the value of the ratio of (surface area of carrier)/(effective volume of liquid), which has been necessary to be not lower than 20 $m^2/m^3$ in the conventional method, can be lowered to about 10 $m^2/m^3$, and moreover various organic waste liquors can be treated in a high BOD removal ratio while maintaining a high BOD load.

As described above, the treating method and apparatus of organic waste water by the methane fermentation according to the present invention are free from the problem in the conventional method, and the present invention has a very high contribution to the development of industry.

What is claimed is:

1. In a method for treating an organic waste water by methane fermentation with the use of an anaerobic fixed bed arranged in an anaerobic treating apparatus, an improvement comprising effecting treatment of said organic waste water in the presence of nickel, iron and cobalt, which are nutrient elements necessary for the proliferation of methane bacteria, while maintaining the amounts of Ni, Fe and Co based on the BOD of said organic waste water to such amounts that the value of the ratio of Ni/BOD is at least $25 \times 10^{-6}$, the value of the ratio of Fe/BOD is at least $60 \times 10^{-6}$ and the value of the ratio of Co/BOD is at least $1.25 \times 10^{-6}$.

2. A method according to claim 1, wherein said anaerobic treating apparatus contains a carrier packed therein, and a value of the ratio of the apparent surface area of the carrier to the effective volume of the apparatus (the ratio of (surface area of carrier)/(effective volume of liquid)) is as low as 10 $m^2/m^3$.

3. The method of claim 2, wherein said organic waste water is treated at a BOD removal ratio of at least 90%.

4. The method of claim 3, wherein said organic waste water is treated at a BOD load of at least 10 kg/$m^3$-day.

5. The method of claim 4, wherein said organic waste water is treated at a BOD load of at least 20 kg/$m^3$-day.

* * * * *